United States Patent [19]

Blattner et al.

[11] Patent Number: 4,492,691
[45] Date of Patent: Jan. 8, 1985

[54] AZATETRACYCLIC CARBONITRILES

[75] Inventors: Hans Blattner, Riehen; Angelo Storni, Rheinfelden, both of Switzerland

[73] Assignee: Ciba-Geigy Corporation, Ardsley, N.Y.

[21] Appl. No.: 394,368

[22] Filed: Jul. 1, 1982

Related U.S. Application Data

[63] Continuation of Ser. No. 212,472, Dec. 3, 1980, abandoned.

[30] Foreign Application Priority Data

Dec. 10, 1979 [CH] Switzerland ............ 10928/79

[51] Int. Cl.³ .................. C07C 491/02; A61K 31/55
[52] U.S. Cl. .................. 424/244; 260/330.9
[58] Field of Search .................. 260/330.9; 424/244

[56] References Cited

U.S. PATENT DOCUMENTS

| | | | |
|---|---|---|---|
| 3,116,283 | 12/1963 | Boller et al. | 260/239 |
| 3,418,339 | 12/1968 | Dobson et al. | 260/239 D X |
| 3,636,045 | 1/1972 | Blattner et al. | 424/274 X |
| 3,636,046 | 1/1972 | Blattner et al. | 424/274 X |
| 3,682,959 | 8/1972 | Blattner et al. | 424/274 X |
| 3,726,897 | 4/1973 | Schindler et al. | 424/274 X |
| 3,749,790 | 7/1973 | Blattner et al. | 424/274 |
| 3,755,357 | 8/1973 | Schindler et al. | 424/274 X |
| 3,772,348 | 11/1973 | Blattner et al. | 424/274 X |
| 3,773,940 | 11/1973 | Schindler et al. | 424/274 |
| 3,777,032 | 12/1973 | Blattner et al. | 424/274 |
| 3,783,161 | 1/1974 | Schindler et al. | 424/274 |
| 3,786,045 | 1/1974 | Blattner et al. | 260/239 D |
| 3,798,237 | 3/1974 | Blattner et al. | 260/332.5 |
| 3,859,439 | 1/1975 | Blattner et al. | 424/274 |
| 3,996,373 | 12/1976 | Blattner | 424/274 |
| 4,002,632 | 1/1977 | van der Berg | 424/263 X |
| 4,112,110 | 9/1978 | Blattner | 424/274 |

FOREIGN PATENT DOCUMENTS

| | | |
|---|---|---|
| 2509617 | 3/1975 | Fed. Rep. of Germany . |
| 2723105 | 12/1977 | Fed. Rep. of Germany . |
| 2723209 | 12/1977 | Fed. Rep. of Germany . |
| 592095 | 10/1977 | Switzerland . |

OTHER PUBLICATIONS

Blattner, et al., C.A., 73, 45491j, (1970).
Burger, Medicinal Chemistry, 2nd Ed., pp. 79–81, (1960), Interscience.
Prinzbach, et al., C.A., 69, 19048t, (1968).
Blattner, et al., C.A., 73, 45488p, (1970).
C.A. 8th Coll. Index, p. 9892S, (1973).

*Primary Examiner*—Joseph Paul Brust
*Attorney, Agent, or Firm*—Irving N. Feit

[57] ABSTRACT

Azatetracyclic carbonitriles of the formula

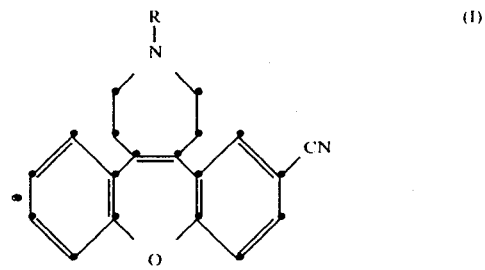

in which R represents hydrogen, lower alkyl, cycloalkyl-lower alkyl having up to 10 carbon atoms, lower alkenyl, lower alkynyl or free, etherified or esterified hydroxy-lower alkyl, and acid addition salts thereof, processes for their manufacture, pharmaceutical compositions that contain such compounds and their use. They are distinguished especially by their central nervous system-depressant, agitation-inhibitory (amphetamine-antagonistic) action. They can therefore be used as tranquillizing, anti-psychotic, agitation-inhibitory compounds for the treatment of agitated states having various causes.

9 Claims, No Drawings

AZATETRACYCLIC CARBONITRILES

This is a continuation of application Ser. No. 212,472 filed on Dec. 3, 1980, now abandoned.

The present invention relates to new azatetracyclic carbonitriles and acid addition salts thereof having valuable pharmacological properties, processes for their manufacture, pharmaceutical compositions that contain the new substances as active substance, and their use.

The azatetracyclic carbonitriles according to the invention correspond to the formula

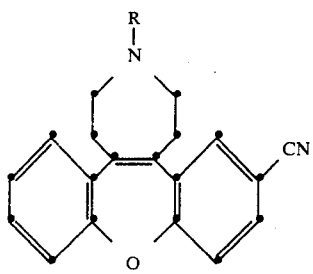

in which R represents hydrogen, lower alkyl, cycloalkyl-lower alkyl having up to 10 carbon atoms, lower alkenyl, lower alkynyl or free, etherified or esterified hydroxy-lower alkyl.

The invention relates also to the acid addition salts of compounds of the formula I, especially the pharmaceutically acceptable acid addition salts.

In the above definition of the formula I and hereinafter lower radicals shall be understood to mean those having a maximum of 8 carbon atoms and preferably a maximum of 4 carbon atoms.

As lower alkyl, R preferably contains from 1 to 6 carbon atoms. These lower alkyl groups, which may be straight-chained or branched, are, for example, methyl, ethyl, propyl, isopropyl, butyl, isobutyl or tert.-butyl.

As cycloalkyl-lower alkyl, the radical R preferably contains from 4 to 8 carbon atoms. Cycloalkyl-lower alkyl is thus, for example, cyclopropylmethyl, cyclobutylmethyl and especially cyclopentylmethyl, cyclohexylmethyl, also, for example, cyclopropylethyl, cyclobutylethyl, cyclopentylethyl, cyclohexylethyl.

As lower alkenyl, the radical R preferably contains 3 or 4 carbon atoms and especially 3 carbon atoms. Lower alkenyl is present, for example, as allyl or 2-methylallyl.

As lower alkynyl, the radical R is especially propargyl.

Where radical R is hydroxy-lower alkyl, the hydroxyl group is separated from the ring nitrogen atom by at least 2 carbon atoms. This radical contains from 2 to 8, and preferably from 2 to 4, carbon atoms. The hydroxy-lower alkyl, which may be straight-chained or branched, is, for example, 1-methyl-2-hydroxyethyl, 2-hydroxypropyl, 1- or 2-methyl-2-hydroxypropyl, and especially 2-hydroxyethyl and 3-hydroxypropyl.

Where radical R is lower alkoxy-lower alkyl, the oxygen atom is separated from the ring nitrogen atom by at least 2 carbon atoms. This radical contains, for example, from 3 to 10, and preferably from 3 to 6, carbon atoms. This lower alkoxy-lower alkyl is, for example, 2-methoxypropyl, 2- or 3-ethoxypropyl, 2- or 3-propoxypropyl, 3-isopropoxypropyl and especially 2-methoxyethyl or 2-ethoxyethyl and more especially 3-methoxypropyl.

Where radical R is alkanoyloxy-lower alkyl, the ester oxygen atom is separated from the ring nitrogen atom by at least 2 carbon atoms. This radical contains, for example, from 3 to 21, and preferably from 4 to 11, carbon atoms. This radical is, for example, 2-formyloxyethyl, 2-acetoxyethyl, 2-propionyloxyethyl, 2-acetoxypropyl, 2-methyl-3-acetoxypropyl or 2- or 3-propionyloxypropyl and especially 3-acetoxypropyl and 3-octanoyloxypropyl.

Salts of compounds of the formula I are especially acid addition salts and more especially pharmaceutically acceptable acid addition salts, for example with inorganic acids, such as hydrochloric acid, hydrobromic acid, sulphuric acid or phosphoric acid, or with organic acids, such as organic carboxylic or sulphonic acids, such as methanesulphonic acid, ethanesulphonic acid, 2-hydroxyethanesulphonic acid, acetic acid, malic acid, tartaric acid, citric acid, lactic acid, oxalic acid, succinic acid, fumaric acid, benzoic acid, salicyclic acid, phenylacetic acid, mandelic acid or embonic acid.

The new azatetracyclic carbonitriles of the general formula I and their acid addition salts exhibit valuable pharmacological properties, for example acting on the central nervous system. They are distinguished especially by their central nervous system-depressant, agitation-inhibitory (amphetamine-antagonistic) action which can be demonstrated with the aid of pharmacological experiments. Thus in rats in an amphetamine-antagonism test (Niemegeers and Janssen, Arzneimittelforsch., Vol. 24, page 45 [1974]) in a dosage range of from 0.01 to 1 mg/kg i.p. or per os. they exhibit an agitation-inhibitory action. The cataleptic action is relatively slight in comparison with the amphetamine-antagonistic action. The new azatetracyclic carbonitriles of the general formula I and their pharmaceutically acceptable acid addition salts can therefore be used as tranquillising, anti-psychotic, agitation-inhibitory compounds for the treatment of agitated states having various causes.

The invention relates especially to compounds of the formula I wherein R represents hydrogen; lower alkyl, for example methyl or ethyl; cycloalkyl-lower alkyl having from 4 to 8 carbon atoms, for example cyclopentylmethyl and cyclohexylmethyl; lower alkenyl, for example allyl; lower alkynyl, for example propargyl; hydroxy-lower alkyl, for example 2-hydroxyethyl and 3-hydroxypropyl; lower alkoxy-lower alkyl, for example 3-methoxypropyl; or alkanoyloxy-lower alkyl, for example acetoxypropyl and octanoyloxypropyl, and to salts thereof, especially acid addition salts and more especially pharmaceutically acceptable acid addition salts.

The invention relates above all to compounds of the formula I wherein R represents lower alkyl, for example methyl or ethyl, or cyclopentylmethyl, such as 7-cyano-3-methyl-2,3,4,5-tetrahydro-1H-dibenz[2,3:6,-7]oxepino[4,5-d]azepine, or 3-(cyclopentylmethyl)-7-cyano-2,3,4,5-tetrahydro-1H-dibenz[2,3:6,7]oxepino[4,5-d]azepine, and to salts thereof, especially acid addition salts and more especially pharmaceutically acceptable acid addition salts.

The compounds of the formula I are prepared in a manner known per se. They are thus obtained, for example by reacting a reactive diester of the diethanol of the formula

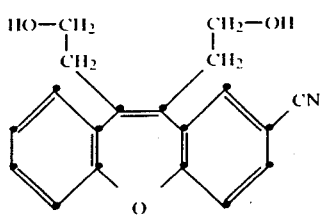

(II)

with a compound of the formula

(III)

As reactive diesters of a diethanol of the formula II it is possible to use esters of strong inorganic acids such as, for example, bis-hydrochloric, bis-hydriodic or especially bis-hydrobromic acid esters or hydrobromic/hydrochloric acid esters. It is also possible to use corresponding diesters of strong organic acids, for example of sulphonic acids, such as methanesulphonic acid, benzenesulphonic acid, p-chlorobenzenesulphonic acid, p-bromobenzenesulphonic acid or p-toluenesulphonic acid. These diesters of compounds of the formula Ii are preferably reacted in a suitable inert solvent at a reaction temperature of from 20° to 130° C. Suitable inert solvents are, for example, hydrocarbons such as benzene or toluene, halohydrocarbons such as chloroform, lower alcohols such as ethanol and especially methanol, ether-type liquids such as ether or dioxan, and lower alkanones, for example acetone, methyl ethyl ketone or diethyl ketone or mixtures of such solvents, for example benzene/methanol.

In the reaction according to the invention of a molar equivalent of a diester of a diethanol of the formula II with a molar equivalent of a free base of the formula III, two molar equivalents of acid are split off which are preferably bonded to an acid-binding agent. Suitable acid binding agents are, for example, alkali metal carbonates, such as potassium carbonate, or, for example, alkali metal hydroxides, such as sodium hydroxide or potassium hydroxide, or excess base of the formula III, also tertiary organic bases, such as pyridine and especially triethylamine or N-ethyl diisopropylamine.

The direct starting materials, that is to say, the reactive diesters of the formula II, can be prepared from the corresponding diethanols by esterification or by replacement of the hydroxy groups with halogen according to the customary methods. The diethanols can in their turn be prepared from the corresponding diacetic acid methyl esters by reduction with lithium aluminium hydride. The diacetic acid methyl esters can be prepared from the corresponding diacetonitriles with methanol and 2 molar equivalents of water with the introduction of hydrogen chloride. The diacetonitriles can in their turn be obtained from the corresponding bis-(bromoethyl) compounds with sodium cyanide.

According to a further process, the compounds of the formula I are obtained by reacting a compound of the formula (IV)

in which Hal represents a halogen atom, with a cyanide compound.

Suitable as radicals Hal in compounds of the formula IV are chlorine or iodine, but preferably bromine. Cyanide compounds are especially alkali metal or heavy metal cyanides. Sodium cyanide is preferred as alkali metal cyanide. More especially suitable, however, is copper(I) cyanide, as a representative of heavy metal cyanides. The reaction can be carried out in the presence or absence of solvents within a temperature range of from 80° to 250°. Suitable solvents are especially pyridine, quinoline, dimethylformamide, 1-methyl-2-pyrrolidinone and hexamethylphosphoric acid triamide. The latter two solvents are especially suitable when using copper(I) cyanide as cyanating agent.

The starting materials of the formula IV are known or can be prepared according to methods known per se such as, for example, analogously to the process first mentioned. In this connection see, i. a. German Offenlegungsschrift No. 2 723 105.

Subsequently to the reactions according to the invention it is possible optionally to carry out a series of conversions that convert compounds of the formula I into different compounds of the formula I.

A compound of the formula I in which the radical R represents hydrogen can optionally be converted into a process product in which R has one of the other meanings.

It is thus possible to carry out, for example, an N-substitution either with a reactive ester of a corresponding alcohol of the formula $R_1$—OH, wherein $R_1$ has the same meaning as R in formula I with the exception of hydrogen, or by a reaction with corresponding aldehydes or ketones under reducing conditions.

The reaction of compounds of the formula I in which R represents hydrogen with a reactive ester of a hydroxy compound of the formula $R_1$—OH is preferably carried out in a solvent at a reaction temperature of from 20° to 130° C., especially at the boiling temperature of the solvent.

As reactive esters it is possible to use, for example, halides, such as chlorides or bromides, also aromatic or aliphatic sulphonic acid esters, such as p-toluenesulphonic acid methyl ester or p-toluenesulphonic acid ethyl ester or methanesulphonic acid methyl ester, methanesulphonic acid ethyl ester, or cyclopentylmethyl esters, or sulphuric acid esters such as, for example, dimethyl or diethyl sulphate. Suitable acid-binding agents are alkali metal carbonates such as, for example, potassium carbonate, or alkali metal hydroxides such as, for example, sodium hydroxide, or tertiary organic bases such as, for example, pyridine or N-ethyl diisopropylamine. Suitable solvents are those solvents that are inert under the reaction conditions, for example hydrocarbons such as benzene or toluene, also alkanols such as, for example, methanol or ethanol, or alkanones such as acetone or methyl ethyl ketone.

Aldehydes and ketones that correspond to the alcohols of the formula $R_1$—OH are, for example, lower aliphatic aldehydes or ketones, lower free, esterified or etherified hydroxyoxyalkanes or esterified oxoalkanecarboxylic acids. The resulting reaction product in the reaction of these aldehydes or ketones with the afore-mentioned compounds of the formula I can be reduced in the same operating cycle or subsequently.

The aldehydes, for example formaldehyde or acetaldehyde, or the ketones, for example acetone, are, for example, heated at from approximately 30° to 100° C. with the afore-mentioned compounds of the formula I in an inert solvent and, at the same time or subsequently, the reaction mixture is hydrogenated with hydrogen in the presence of a catalyst. Suitable solvents are, for example, alkanols, such as methanol or ethanol, and suitable catalysts are noble metal catalysts such as palladium-on-carbon.

Instead of using hydrogen in the presence of a catalyst, it is possible, however, to use for the reductive alkylation also other reducing agents, for example, formic acid. According to this variant of the process, the afore-mentioned compounds of the formula I are heated with formic acid and the afore-mentioned types of aldehydes or ketones, especially formaldehyde, preferably without a solvent.

Further, a compound of the formula I in which the radical R represents a hydroxy-lower alkyl group, can optionally be acylated to form a compound in which the radical R represents an esterified hydroxy-lower alkyl group.

The acylation can be carried out, for example, with a carboxylic acid anhydride or with a corresponding carboxylic acid halide at a reaction temperature of between approximately 20° and 100° C. As the condensation takes place with the splitting off of acid, it is advantageous to add to the reaction mixture an acid-binding agent, for example a tertiary organic base such as pyridine. Excess tertiary organic base can also be used as solvent. It is also possible to use as solvent hydrocarbons, for example benzene or toluene, or halohydrocarbons, for example chloroform.

Further, a compound of the formula I in which R is different from hydrogen can optionally be converted into a process product in which the radical R represents hydrogen. This is achieved advantageously by replacing this group R, preferably a group that can readily be split off, such as the methyl or allyl group, by a radical that can be split off by means of reduction, including hydrogenolysis, especially by means of reaction with a haloformic acid 2-arylalkyl ester or a haloformic acid 2-haloalkyl ester, by a 2-arylalkoxycarbonyl radical, for example the benzyloxycarbonyl radical, or by a 2-haloalkoxycarbonyl radical, for example the 2,2,2-trichloroethoxycarbonyl radical, and replacing this radical with hydrogen by means of hydrogenolysis or reduction in the customary manner. 2-Arylalkoxycarbonyl radicals can be removed by hydrogenation, for example, by means of hydrogen in the presence of a hydrogenation catalyst, for example platinum, palladium or Raney nickel, and optionally in the presence of hydrogen chloride, at room temperature and normal pressure or at moderately elevated temperatures and pressures, and in suitable organic solvents such as, for example, methanol, ethanol or dioxan. 2-Haloalkoxycarbonyl radicals such as, for example, the 2-iodoethoxycarbonyl radical or 2,2,2-tribromoethoxycarbonyl radical, in addition to the 2,2,2-trichloroethoxycarbonyl radical, can be removed especially by metallic reduction (so-called nascent hydrogen). Nascent hydrogen can be obtained by the action of metal or metal alloys, such as amalgams, on agents that yield hydrogen, such as carboxylic acids, alcohols or water, zinc or zinc alloys together with acetic acid being especially suitable. 2-Haloalkoxycarbonyl radicals can also be split off reductively by chromium(II) compounds such as chromium(II) chloride or chromium(II) acetate.

Depending upon the conditions of the process and the starting materials, the end products are obtained optionally in free form or in the form of their salts, which can be converted into one another or into different salts in the customary manner. Thus, free compounds of the formula I are formed from resulting acid addition salts, for example by treating with bases or basic ion exchangers, while free bases of the formula I are converted into acid addition salts, for example by reacting with organic or inorganic acids, especially with those that are suitable for the formation of pharmaceutically acceptable salts, such as those mentioned above.

Salts of the new compounds can also be used for purification purposes, for example by converting the free compounds into their salts, isolating and optionally purifying these salts and converting them into the free compounds again. As a result of the close relationships between the new compounds in free form and in the form of their salts, hereinbefore and hereinafter the free compounds shall be understood to mean optionally also the corresponding salts where appropriate with regard to meaning and purpose.

Resulting racemates may be separated into the antipodes according to methods known per se, for example by recrystallizing from an optically active solvent, by treating with suitable micro-organisms or by reacting with an optically active substance, especially an acid, that forms salts with the racemic compound and separating the salt mixture obtained in this manner, for example on the basis of different solubilities, into the diastereoisomeric salts, from which the free antipodes can be liberated by the action of suitable agents. Optically active acids that are especially customary are, for example, the D-form and L-form of tartaric acid, di-O,O'-p-toluolyltartaric acid, malic acid, mandelic acid, camphorsulphonic acid, glutamic acid, aspartic acid or quinic acid. Advantageously, the more effective of the two antipodes is isolated.

The invention relates also to those forms of the process in which a compound obtainable as intermediate at any stage of the process is used as starting material and the remaining process steps are carried out, or the process is discontinued at any stage, or in which a starting material is formed under the reaction conditions, or in which a reactant is present optionally in the form of its salt.

Advantageously, the starting materials used for carrying out the process according to the invention are those which result in the groups of end products given special mention at the beginning, and particularly the end products especially described and pointed out.

The new compounds can be used, for example, in the form of pharmaceutical preparations, which contain an active quantity of active substance, optionally together with inorganic or organic, solid or liquid pharmaceutically acceptable carriers that are suitable for enteral, for example oral, or parenteral administration. Tablets or gelatin capsules are thus used which contain the active substance together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol. Tablets likewise contain binders, for example magnesium aluminium silicate, starches, such as corn, wheat, rice or arrowroot starch, gelatin, tragacanth, methylcellulose, sodium carboxymethoxycellulose and/or polyvinylpyrrolidone, and, if desired, disintegrating agents, for example starches, agar, alginic acid or a salt thereof, such as sodium alginate, and/or effervescent mixtures, or adsorbents, colourants, flavourings and sweeteners. It is further possible to use the new pharmacologically active compounds in the form of injectable, for example intravenously administrable, preparations or infusion solutions. Such solutions are preferably isotonic aqueous solutions or suspensions, it being possible to prepare these before use, for example in the form of lyophilised preparations, which contain the active substance alone or together with a carrier, for example mannitol. The pharmaceutical preparations can be sterilised and/or contain adjuncts, for example, preservatives, stabilisers, wetting agents and/or emulsifiers, solubilisers, salts for the regulation of the osmotic pressure and/or buffers. The present pharmaceutical preparations, which, if desired, can contain further pharmacologically valuable substances, are manufactured in a manner known per se, for example by means of conventional mixing, granulating, coating, dissolving or lyophilising processes, and contain from approximately 0.1% to 100%, especially from approximately 1% to approximately 50%, and in the case of lyophilisates up to 100% of active substance. The dosage depends on the mode of administration, and on the species, age and individual condition. The daily doses of the free bases or of pharmaceutically acceptable salts thereof lie between approximately 0.01 mg/kg and 0.5 mg/kg for warm-blooded animals in general and from approximately 0.001 g to approximately 0.01 g for warm-blooded animals weighing approximately 70 kg.

The following Examples serve to illustrate the invention. Temperature are given in degrees Centigrade.

EXAMPLE 1

In a nitrogen atmosphere, a mixture of 18.5 g (0.05 mol) of 7-bromo-3-methyl-2,3,4,5-tetrahydro-1H-dibenz[2,3:6,7]oxepino[4,5-d]azepine and 5.35 g (0.06 mol) of copper(I) cyanide in 20 ml of dimethylformamide is heated at 180°, while stirring, for 24 hours. The mixture is then cooled to 30° and diluted with 100 ml of methylene chloride, and 50 ml of a 50% aqueous ethylenediamine solution are added thereto. The organic phase is subsequently separated off, washed with water and, after drying over sodium sulphate, is concentrated by evaporation. After recrystallisation from acetone the crystalline residue, the 7-cyano-3-methyl-2,3,4,5-tetrahydro-1H-dibenz[2,3:6,7]oxepino[4,5-d]azepine melts at 181°-183°.

For conversion into the methanesulphonate, 12.1 g (0.04 mol) thereof are dissolved in 250 ml of acetone and, while stirring, 3.84 g of methanesulphonic acid are added to this solution, whereupon the 7-cyano-3-methyl-2,3,4,5-tetrahydro-1H-dibenz[2,3:6,7]oxepino[4,5-d]azepine-methanesulphonate having a melting point of 265°-268° crystallises out.

The starting material may be prepared in the following manner:

A mixture of 560.0 g of 2-(4-bromophenoxy)benzoic acid in 1940 ml of absolute benzene, 218 ml of absolute ethanol and 32.6 ml of concentrated sulphuric acid is boiled under reflux for 32 hours, the water that forms being removed in a water separator. The reaction mixture is cooled to 10° and, with the addition of ice, is washed with 1000 ml of water, 500 ml of a 2N aqueous sodium carbonate solution and then once more with 1000 ml of water. The organic phase is separated off, dried over magnesium sulphate and concentrated by evaporation at 40° at a pressure of 11 mm Hg. The residue is distilled in a high vacuum and yields the 2-(4-bromophenoxy)benzoic acid ethyl ester. Boiling point 140°-150°/0.05 mm Hg.

A solution of 477.0 g of the 2-(4-bromophenoxy)benzoic acid ethyl ester in 900 ml of absolute diethyl ether is introduced dropwise into 42.3 g of lithium aluminium hydride in 500 ml of diethyl ether over a period of 1 hour while passing a stream of nitrogen through the mixture. The reaction mixture is boiled under reflux for 6 hours, cooled to form 0° to 5° and, while passing nitrogen through it, 450 ml of acetic acid ethyl ester are added and then 350 ml of water are added carefully. The precipitate is filtered off and is subsequently washed with diethyl ether. The aqueous phase of the filtrate is separated off and washed with 100 ml of diethyl ether; the combined organic phases are dried over magnesium sulphate and concentrated by evaporation to dryness under 11 mm Hg. The 2-(4-bromophenoxy)-benzyl alcohol remaining behind is in the form of a colourless oil.

A mixture of 413.0 g of the 2-(4-bromophenoxy)benzyl alcohol and 1290 ml of 48% hydrobromic acid is boiled under reflux for 4 hours, then cooled and poured onto 2000 ml of ice and water. The greenish oil that separates out is dissolved in 2000 ml of diethyl ether. The organic phase is washed twice with 400 ml of water and with 400 ml of a 1N aqueous sodium bicarbonate solution, dried over magnesium sulphate and concentrated by evaporation at 40° under 11 mm Hg. The 2-(4-bromophenoxy)benzyl bromide, obtained in the form of an oily residue, is used without purification.

457.8 g of the crude 2-(4-bromophenoxy)benzyl bromide are added over a period of one hour to a mixture that is boiling under reflux of 171.0 g of sodium cyanide in 160 ml of water and 44 ml of ethanol; at the same time 362 ml of ethanol are added dropwise. The mixture is subsequently boiled under reflux for a further 3 hours and then diluted with 1500 ml of water. The aqueous ethanolic phase is washed with 1000 ml of diethyl ether and the ether phase is separated off, washed twice with 200 ml of water, dried over magnesium sulphate and concentrated to dryness under 11 mm Hg. The residue is crystallised from a mixture of diethyl ether and petroleum ether and yields 2-(4-bromophenoxy)phenyl acetonitrile.

Melting point 56°-58°.

25.3 g of sodium are dissolved, while stirring, in 400 ml of absolute ethanol and then approximately 200 ml of absolute ethanol are distilled off again from the reaction mixture. 1500 ml of absolute toluene are then added and distillation is continued under a Vigreux column until the boiling point has reached 108° whereupon the sodium ethylate crystallises out. At from 100° to 110°, a mixture of 288 g (1 mol) of 2-(4-bromophenoxy)phenyl acetonitrile and 354 g (3 mol) of diethyl carbonate are then added dropwise, over a period of 1 hour, while distilling off simultaneously the ethanol that is formed.

After the dropwise addition has been completed distillation of the reaction mixture is continued until the boiling point has again reached from 108° to 110°. The reaction mixture is subsequently cooled to room temperature, diluted with 300 ml of absolute toluene, and 170 g (1.2 mol) of methyl iodide are added dropwise, over a period of one hour. To complete the reaction, the mixture is stirred for a further one hour at room temperature and 5 hours at 80°. After cooling to room temperature, 1 liter of water is added, and the organic phase is separated off, washed with water and, after drying over sodium sulphate, is completely concentrated by evaporation in vacuo. The crude 2-(4-bromophenoxy)phenyl-α-methylcyanoacetic acid ethyl ester remains as residue.

374 g (1 mol) of crude 2-(4-bromophenoxy)phenyl-α-methylcyanoacetic acid ethyl ester, 830 ml of 96% ethanol and 460 ml of 50% aqueous caustic potash solution are boiled under reflux, while stirring well, for 24 hours. The reaction mixture is then concentrated by evaporation under 11 mm Hg at 50° and the residue is dissolved in 3500 ml of water. After filtering under clear, the alkaline solution is acidified with concentrated hydrochloric acid and the 2-(4-bromophenoxy)phenyl-α-methylacetic acid crystallises out. After filtering off, the resulting acid is dried in vacuo at 50° and then recrystallised from acetonitrile. Melting point 99°–101°.

321 g (1 mol) of 2-(4-bromophenoxy)phenyl-α-methylacetic acid and 3210 g of polyphosphoric acid are heated for one hour at from 100° to 105° while stirring well. While stirring, the reaction mixture is subsequently poured into 3 liters of water, the temperature being maintained at below 10° by the addition of ice. The oil that separates out is extracted with diethyl ether and the organic phase is washed with water, dried over potassium carbonate and concentrated. After cooling, the 8-bromo-11-methyldibenz[b,f]oxepin-10(11H)-one having a melting point of from 85° to 87° crystallises out.

A solution of 303 g (1 mol) of 8-bromo-11-methyldibenz[b,f]oxepin-10(11H)-one in 1500 ml of absolute toluene is added dropwise, over a period of 5 hours and while stirring well, to a Grignard solution prepared from 49 g (2 mol) of magnesium, 450 ml of absolute ether and 284 g of methyl iodide, there being maintained a reaction temperature of from −5° to 0°. The reaction mixture is subsequently heated to 55° and stirring is continued for 15 hours at this temperature. The reaction mixture is then cooled to 0° and, while stirring, poured onto a solution of 680 g of ammonium chloride in 2000 ml of ice water. The organic phase is separated off and the aqueous phase is extracted with toluene. The combined organic solutions are washed with water, dried over sodium sulphate and concentrated by evaporation in vacuo. The 8-bromo-10,11-dimethyldihydrodibenz[b,f]oxepin-10-ol in the form of an oil remains as residue.

319 g (1 mol) of 8-bromo-10,11-dimethyldihydrodibenz[b,f]oxepin-10-ol (crude product) and 1.5 g of p-toluenesulphonic acid are heated in a distillation apparatus under 11 mm Hg for 1 hour at 180° and for 5 hours at 200° external temperature, during which water is split off. The distillation receiver is then exchanged and the resulting 2-bromo-10,11-dimethyldibenz[b,f]oxepin is distilled in a high vacuum, boiling point 142°–148°/0.01 torr. The light yellow distillate is dissolved in 300 ml of acetonitrile, the solution is cooled to 0° and the product crystallises out.

Melting point 117°–119°.

30.1 g (0.1 mol) of 2-bromo-10,11-dimethyldibenz[b,f]oxepin are dissolved in 525 ml of carbon tetrachloride and 35.6 g (0.2 mol) of N-bromosuccinimide are added to this solution. While stirring and in a nitrogen atmosphere, the mixture is heated to boiling under the illumination of a UV-lamp. Boiling of the mixture is maintained until all the N-bromosuccinimide lying on the bottom of the vessel has been converted into succinimide floating on the solution, this taking approximately 10 minutes. The reaction mixture is then cooled to 20° and the succinimide is separated off by filtration. The filtrated is washed with water, dried over sodium sulphate and concentrated in vacuo. On cooling, the 2-bromo-10,11-bis(bromomethyl)dibenz[b,f]oxepin having a melting point of from 124° to 126° crystallises out.

While stirring and in a nitrogen atmosphere, 45.9 g (0.1 mol) of 2-bromo-10,11-bis(bromomethyl)dibenz[b,f]oxepin are suspended in 500 ml of acetonitrile. A solution of 11.8 g (0.24 mol) of sodium cyanide in 36 ml of distilled water is added dropwise to this suspension over a period of 10 minutes. The mixture is then stirred for a further 1½ hours, the internal temperature being maintained at 20° by cooling slightly. After this time all the starting material has reacted and a brown solution has been produced. This reaction solution is washed with water and concentrated in vacuo and the 2-bromodibenz[b,f]oxepin-10,11-diacetonitrile having a melting point of from 241° to 243° crystallises out.

35.1 g (0.1 mol) of 2-bromodibenz[b,f]oxepin-10,11-diacetonitrile are suspended, while stirring, in 400 ml of methanol and 3.6 ml of water and cooled in an ice bath to from 0° to 5°. Dry hydrogen chloride is then introduced until saturation is reached. The reaction mixture is stirred for a further 12 hours at 20° and then boiled under reflux for 24 hours. The reaction solution is subsequently concentrated by evaporation in vacuo and the residue is extracted with ether. The organic phase is separated off, washed with water and 2N soda solution, dried over sodium sulphate and concentrated by evaporation. The crude 2-bromodibenz[b,f]oxepin-10,11-diacetic acid methyl ester remaining behind is in the form of a yellow oil.

In a nitrogen atmosphere and in the absence of water, a suspension of 11.4 g (0.3 mol) of lithium aluminium hydride in 750 ml of absolute diethyl ether is slowly added, while stirring, to an ice-cooled solution of 40 g (0.3 mol) of anhydrous aluminium chloride in 1 liter of absolute diethyl ether in such a manner that the reaction temperature does not exceed 5°. Subsequently at from −2° to +3° a solution of 41.7 g (0.1 mol) of crude 2-bromodibenz[b,f]oxepin-10,11-diacetic acid methyl ester in 300 ml of absolute diethyl ether is added dropwise over a period of 30 minutes. After the dropwise addition has been completed the reaction mixture is stirred for a further 17 hours at room temperature, then cooled to from 0° to 5° and the excess aluminium hydride is destroyed carefully by the dropwise addition of 100 ml of water. The organic phase is then separated off, washed twice using 300 ml of water each time, dried over sodium sulphate and concentrated by evaporation. The crude 2-bromodibenz[b,f]oxepin-10,11-diethanol in the form of a yellow oil remains as residue.

36.1 g (0.1 mol) of crude 2-bromodibenz[b,f]oxepin-10,11-diethanol are dissolved in 120 ml of pyridine at room temperature and, in an ice/sodium chloride bath, 25.2 g (0.22 mol) of methanesulphochloride are added dropwise, while stirring, at a reaction temperature of −5°. The reaction mixture is subsequently stirred for 30 minutes at 0° and for 2 hours at from 15° to 25°. Thereafter, the reaction mixture is washed, together with methylene chloride, in a separating funnel in succession with in each case 800 ml of 2N hydrochloric acid and of water, dried over sodium sulphate and concentrated by evaporation in vacuo. The crude 2-bromo-10,11-bis-[2-(methylsulphonyloxy)ethyl]-dibenz[b,f]oxepin in the form of a light brown oil remains as residue.

51.7 g (0.1 mol) of crude 2-bromo-10,11-bis-[2-(methylsulphonyloxy)ethyl]-dibenz[b,f]oxepin are stirred with a solution of 60 g (1.36 mol) of methylamine in 350 ml of ethanol for 3 hours at an internal temperature or 60°, crystals slowly separating out after 30 minutes. The reaction mixture is subsequently cooled in an ice bath, the resulting crystals are filtered off by suction and are washed with ethanol. After drying at 80° in a vacuum chamber, the suction-filtered material, the 7-bromo-3-methyl-2,3,4,5-tetrahydro-1H-dibenz[2,3:6,7]oxepino[4,5-d]azepine melts at from 189° to 192°.

EXAMPLE 2

7-Cyano-3-(cyclopentylmethyl)-2,3,4,5-tetrahydro-1H-dibenz[2,3:6,7]oxepino[4,5-d]azepine having a melting point of from 99° to 102° (from acetonitrile) is obtained from 20.6 g (0.05 mol) of 7-bromo-3-(cyclopentylmethyl)-2,3,4,5-tetrahydro-1H-dibenz[2,3:6,7]oxepino[4,5-d]azepine and 5.35 g (0.06 mol) of copper(I) cyanide in 20 ml of dimethylformamide in a manner analogous to that of Example 1. The methanesulphonate melts at from 266° to 269° (from ethanol).

The starting material, 7-bromo-3-(cyclopentylmethyl)-2,3,4,5-tetrahydro-1H-dibenz[2,3:6,7]oxepino[4,5-d]azepine, is prepared from 51.7 g (0.01 mol) of crude 2-bromo-10,11-bis-[2-(methylsulphonyloxy)ethyl]-dibenz[b,f]oxepin and 29.7 g (0.3 mol) of (aminomethyl)cyclopentane in 100 ml of ethanol in a manner analogous to that of the last section of Example 1. Melting point 125° to 128° (from acetonitrile).

EXAMPLE 3

0.2 g of anhydrous potassium carbonate are added to a stirred solution of 6.0 g (0.02 mol) of 7-cyano-3-methyl-2,3,4,5-tetrahydro-1H-dibenz[2,3:6.7]oxepino[4,5-d]azepine in 100 ml of absolute benzene and subsequently a solution of 5.1 g (0.024 mol) of chloroformic acid trichloroethyl ester in 20 ml of absolute benzene is added dropwise thereto at a temperature of from 20° to 25°. The reaction mixture is subsequently stirred at room temperature for 16 hours and then 20 ml of 5% ammonia are added thereto. The organic phase is separated off, washed with 5% aqueous methanesulphonic acid and, after drying over sodium sulphate, is concentrated to a small volume, whereupon the 7-cyano-2,3,4,5-tetrahydro-1H-dibenz[2,3:6,7]oxepino[4,5-d]azepine-3-carboxylic acid trichloroethyl ester having a melting point of 178° to 180° crystallises out. 4.6 g (0.01 mol) of 7-cyano-2,3,4,5-tetrahydro-1H-dibenz[2,3:6,7]oxepino[4,5-d]azepine-3-carboxylic acid trichloroethyl ester are dissolved in 700 ml of 90% acetic acid and at 35°, 6.8 g of zinc dust are added, the whole quantity at once. This mixture is stirred for 6 hours at room temperature and subsequently is completely concentrated by evaporation in a rotary evaporator. While cooling with ice, 100 ml of concentrated ammonia are added to the residue and the resulting base is extracted with methylene chloride. The organic phase is separated off, washed with ether, dried over sodium sulphate and concentrated by evaporation. The oily residue is dissolved in 10 ml of ethanol and this solution is neutralised with methanesulphonic acid, whereupon the 7-cyano-2,3,4,5-tetrahydro-1H-dibenz[2,3:6,7]oxepino[4,5-d]azepine-methanesulphonate crystallises out, which, after recrystallization from methanol, melts at from 219° to 222°.

EXAMPLE 4

Tablets containing 0.002 g of 7-cyano-3-methyl-2,3,4,5-tetrahydro-1H-dibenz[2,3:6,7]oxepino[4,5-d]azepine-methanesulphonate are manufactured as follows:

| Composition (for 10 000 tablets): | |
|---|---|
| 7-cyano-3-methyl-2,3,4,5-tetrahydro-1H—dibenz[2,3:6,7]oxepino[4,5-d]azepine-methanesulphonate | 20.00 g |
| lactose | 380.80 g |
| potato starch | 354.70 g |
| stearic acid | 10.00 g |
| talc | 200.00 g |
| magnesium stearate | 2.50 g |
| colloidal silica | 32.00 g |
| ethanol | q.s. |

A mixture of the 7-cyano-3-methyl-2,3,4,5-tetrahydro-1H-dibenz[2,3:6,7]oxepino[4,5-d]azepine-methanesulphonate, the lactose and 194.70 g of potato starch is wetted with an ethanolic solution of the stearic acid and is granulated through a sieve. After drying, the remainder of the potato starch, the talc, the magnesium stearate and the colloidal silica are admixed and the mixture is pressed into tablets each weighing 0.1 g which, if desired, may be provided with dividing notches for a more precise adaptation of the dose.

EXAMPLE 5

Dragées containing 0.005 g of the methanesulphonic acid salt of 7-cyano-3-(cyclopentylmethyl)-2,3,4,5-tetrahydro-1H-dibenz[2,3:6,7]oxepino[4,5-d]azepine are manufactured as follows:

| Composition (for 10 000 dragees): | |
|---|---|
| methanesulphonic acid salt of 7-cyano-3-(cyclopentylmethyl)-2,3,4,5-tetrahydro-1H—dibenz[2,3:6,7]oxepino[4,5-d]-azepine | 50.00 g |
| lactose | 175.90 g |
| stearic acid | 10.00 g |
| colloidal silica | 56.60 g |
| talc | 165.00 g |
| potato starch | 20.00 g |
| magnesium stearate | 2.50 g |
| saccharose (crystalline) | 502.28 g |
| shellac | 6.00 g |
| gum arabic | 10.00 g |
| colourant | 0.22 g |
| titanium dioxide | 1.50 g |
| ethanol | q.s. |

A granulate is prepared from the 7-cyano-3-(cyclopentylmethyl)-2,3,4,5-tetrahydro-1H-dibenz[2,3:6,7]oxepino[4,5-d]azepine-methanesulphonate, the lactose and an ethanolic solution of the stearic acid and, after drying, is mixed with the colloidal silica, the talc, the potato starch and the magnesium stearate and pressed into dragée cores. These are subsequently coated with a concentrated syrup of the saccharose, the shellac, the gum arabic, the colourant and the titanium dioxide and dried. There are thus obtained dragées each weighing 0.1 g and each containing 0.005 g of active substance.

EXAMPLE 6

Capsules containing 0.002 g of the 7-cyano-3-methyl-2,3,4,5-tetrahydro-1H-dibenz[2,3:6,7]oxepino[4,5-d]azepine-methanesulphonate are manufactured as follows:

| Composition (for 1000 capsules) | |
| --- | --- |
| 7-cyano-3-methyl-2,3,4,5-tetrahydro-1H—dibenz[2,3:6,7]oxepino[4,5-d]-azepine-methanesulphonate | 2.00 g |
| lactose | 271.00 g |
| gelatin | 2.00 g |
| corn starch | 10.00 g |
| talc | 15.00 g |
| water | q.s. |

The 7-cyano-3-methyl-2,3,4,5-tetrahydro-1H-dibenz[2,3:6,7]oxepino[4,5-d]azepine-methanesulphonate is mixed with the lactose, the mixture is wetted uniformly with an aqueous solution of the gelatin and granulated through a suitable sieve (for example a sieve having an interior mesh width of from 1.2 to 1.5 mm). The granulate is mixed with the dried corn starch and the talc and is introduced uniformly into the hard gelatin capsules (size 1).

EXAMPLE 7

An aqueous injection solution containing 0.001 g/ml of 7-cyano-3-methyl-2,3,4,5-tetrahydro-1H-dibenz[2,3:6,7]oxepino[4,5-d]azepine-methanesulphonate is manufactured as follows:

| Composition (for 1000 ampoules) | |
| --- | --- |
| 7-cyano-3-methyl-2,3,4,5-tetrahydro-1H—dibenz[2,3:6,7]oxepino[4,5-d]azepine-methanesulphonate | 1.00 g |
| water | q.s. |

A solution of the 7-cyano-3-methyl-2,3,4,5-tetrahydro-1H-dibenz[2,3:6,7]oxepino[4,5-d]azepine-methanesulphonate in 1000 ml of water is introduced into ampoules and sterilised. One ampoule contains a 0.1% solution of the active substance.

What is claimed is:

1. A compound of the formula I

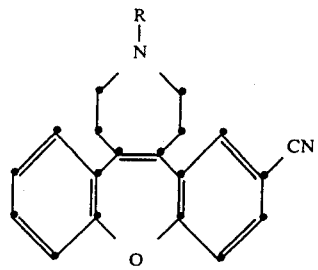

wherein R represents lower alkyl having from 1 to 4 carbon atoms or cyclopentylmethyl and pharmaceutically acceptable salts thereof.

2. 7-cyano-3-methyl-2,3,4,5-tetrahydro-1H-dibenz[2,3:6,7]oxepino[4,5-d]azepine and pharmaceutically acceptable acid addition salts of this compound.

3. 3-(cyclopentylmethyl)-7-cyano-2,3,4,5-tetrahydro-1H-dibenz[2,3:6,7]oxepino[4,5-d]azepine and pharmaceutically acceptable acid addition salts of this compound.

4. A pharmaceutical composition useful in the treatment of agitated states in a warmblooded animal, comprising a therapeutically effective amount of a compound according to claim 1 or a pharmaceutically acceptable acid addition salt thereof, and at least one pharmaceutical carrier.

5. A pharmaceutical composition according to claim 4, which contains 7-cyano-3-methyl-2,3,4,5-tetrahydro-1H-dibenz[2,3:6,7]oxepino[4,5-d]azepine or a pharmaceutically acceptable acid addition salt thereof, and at least one pharmaceutical carrier.

6. A pharmaceutical composition according to claim 4, which contains 3-(cyclopentylmethyl)-7-cyano-2,3,4,5-tetrahydro-1H-dibenz[2,3:6,7]oxepino[4,5-d]azepine or a pharmaceutically acceptable acid addition salt thereof, and at least one pharmaceutical carrier.

7. A method of treatment of agitated states in a warmblooded animal, which comprises administering to said animal a therapeutically effective amount of a compound according to claim 1, or a pharmaceutically acceptable salt of such a compound.

8. A method according to claim 7, which comprises administering a therapeutically effective amount of 7-cyano-3-methyl-2,3,4,5-tetrahydro-1H-dibenz[2,3:6,7]oxepino[4,5-d]azepine or a pharmaceutically acceptable salt of such a compound.

9. A method according to claim 7, which comprises administering a therapeutically effective amount of 3-(cyclopentylmethyl)-7-cyano-2,3,4,5-tetrahydro-1H-dibenz[2,3:6,7]oxepino[4,5-d]azepine or pharmaceutically acceptable salt of such a compound.

* * * * *